(12) United States Patent
Archambault et al.

(10) Patent No.: US 8,414,933 B2
(45) Date of Patent: Apr. 9, 2013

(54) BRASSOCATTLEYA MARCELLA KOSS ORCHID EXTRACT AND USE THEREOF AS SKIN DEPIGMENTATION AGENT

(75) Inventors: Jean-Christophe Archambault, Meung S/Loire (FR); Jean Hubert Cauchard, Orleans (FR); Kristell Lazou, Orleans (FR); Frederic Bonte, Orleans (FR)

(73) Assignee: L V M H Recherche, Saint Jean de Braye (FR)

( * ) Notice: Subject to any disclaimer, the term of this patent is extended or adjusted under 35 U.S.C. 154(b) by 0 days.

(21) Appl. No.: 12/382,251

(22) Filed: Mar. 11, 2009

(65) Prior Publication Data

US 2009/0232758 A1 Sep. 17, 2009

(30) Foreign Application Priority Data

Mar. 13, 2008 (FR) ...................... 08 51642

(51) Int. Cl.
*A61K 36/00* (2006.01)
*A61K 8/02* (2006.01)

(52) U.S. Cl.
USPC ........................... 424/725; 424/401; 514/783

(58) Field of Classification Search .................. None
See application file for complete search history.

(56) References Cited

FOREIGN PATENT DOCUMENTS

| DE | 198 06 947 A1 | 8/1999 |
|---|---|---|
| EP | 1566168 A1 * | 8/2005 |
| FR | 2 784 027 | 4/2000 |
| JP | 2-279618 | 11/1990 |
| JP | 2002-145730 | 5/2002 |
| JP | 2004-67549 | 3/2004 |
| WO | WO 99/22707 A1 | 5/1999 |
| WO | WO 99/24035 A1 | 5/1999 |
| WO | WO 2004/093839 A1 | 11/2004 |

OTHER PUBLICATIONS

RD 480011A, Apr. 2004, RD, Lintner.*
French Search Report issued on Nov. 27, 2008 for application No. FR 08/51642.
Snyder, "Classification of the Solvent Properties of Common Liquids," *Journal of Chromatography*, vol. 92, 1974, pp. 223-230.
Abruzzo et al., "Validation of oligonucleotide microarray data using microfluidic low-density arrays: a new statistical method to normalize real-time RT-PCR data," *BioTechniques*, vol. 38, No. 5, 2005, pp. 785-792.
Slominski et al., "Melanin Pigmentation in Mammalian Skin and Its Hormonal Regulation," *Physiol. Review*, vol. 84, 2004, pp. 1155-1228.
Van Den Bossche et al., "The Quest for the Mechanism of Melanin Transfer," *Traffic*, vol. 7, 2006, pp. 769-778.
Schiaffino et al., "The ocular albinism type 1 (OA1) protein and the evidence for an intracellular signal transduction system involved in melanosome biogenesis," *Pigment Cell Res.*, vol. 18, 2005, pp. 227-233.
Jimbow et al., "Assembly, Target-Signaling and Intracellular Transport of Tyrosinase Gene Family Proteins in the Initial Stage of Melanosome Biogenesis," *Pigment Cell Res.*, vol. 13, 2000, pp. 222-239.

* cited by examiner

*Primary Examiner* — Patricia Leith
(74) *Attorney, Agent, or Firm* — Foley & Lardner LLP

(57) ABSTRACT

This invention relates to an orchid extract of the *Brassocattleya marcella* Koss variety, as well as the use thereof in compositions such as cosmetic compositions, intended to depigment the skin, in particular to lighten the complexion or to improve the uniformity of the skin coloring, or to correct or attenuate skin spots or hyperpigmented skin areas.

13 Claims, No Drawings

BRASSOCATTLEYA MARCELLA KOSS ORCHID EXTRACT AND USE THEREOF AS SKIN DEPIGMENTATION AGENT

This invention relates to an orchid extract of the *Brassocattleya Marcella* Koss species, as well as the use thereof in compositions, such as cosmetic compositions, intended to depigment the skin, in particular to lighten the complexion or improve the uniformity of the skin coloring, or to correct or attenuate skin pigment spots or hyperpigmented areas of the skin.

In humans, pigmentation results from the synthesis and distribution of melanin pigments in the skin, the follicles or the hair. It is regulated by numerous internal or external factors.

Hyperpigmentation of the skin is a common disorder manifested by the appearance of brown or colored spots on skin fragments in various parts of the body, in particular on the backs of the hands, the face, the neckline or even the head in men.

External factors, such as exposure to ultraviolet rays, or natural situations, such as aging or sudden hormonal changes, can cause these skin pigmentation defects.

To deal with the appearance of these spots, controlling pigmentation by means capable of attenuating these unaesthetic signs is therefore an important challenge in the field of cosmetics and in particular skin cosmetics.

The treatment of pigmented spots can involve techniques such as liquid nitrogen application (cryotherapy) or the use of lasers—techniques that are not always satisfactory or the use of depigmenting substances.

These depigmenting substances and techniques are thus used in particular:

- for aesthetic or cosmetic purposes, in compositions intended to improve the homogeneity of the skin color or to lighten the complexion.
- to correct or attenuate skin pigment spots, in particular those consisting of various skin discolorations, in particular the skin effects of photodermatoses, pigmentation induced by contact dermatoses or drug-induced photodermatoses, melasma, keratoses, for example senile or actinic keratosis, senile lentigo (age spots), solar lentigo, the lasting effects of burns, such as sunburns or other skin injuries, or scars, spots due to allergic or phototoxic reactions, dermatitis or other such small pigmented lesions; or to correct or attenuate the edge of depigmented areas caused by certain types of leucoderma such as vitiligo.

The depigmenting substances known are in particular hydroquinone and derivatives thereof, ascorbic acid and derivatives thereof, placental extracts, kojic acid, arbutin, iminophenols (WO 99/22707), the combination of carnitine and quinone (DE 19806947), amino phenol amide derivatives (FR 2 772 607), and benzothiazole derivatives (WO 99/24035). These substances may have certain disadvantages, be unstable, require use at high concentrations, lack specificity with regard to their mode of action, or have a cytotoxic or irritating activity.

The search for new effective non-toxic depigmenting substances is therefore a cosmetic necessity.

Orchids, of the Orchidaceae family, including 25,000 species distributed among 850 genera, are among the plants most widely studied for the cosmetic properties of their extracts.

For example, JP 2004-067549 discloses the use of orchids of the *Cattleya* and *Brassocattleya* genera as a bleaching depigmenting agent in cosmetic compositions.

The cross-breeding of two natural orchid genera, the *Brassavola* genus and the *Cattleya* genus, results in plants of a sub-genus: "*Brassocattleya*". Among these, the orchid of the *Brassocattleya Marcella* Koss species, also called Pink Marvel®, was previously known for the beauty and color of its flowers, and cultivated for its ornamental qualities. No study has specifically evaluated the properties of this genus for cosmetic purposes.

However, the inventors demonstrated in their research that an orchid extract of the *Brassocattleya Marcella* Koss species is capable of inhibiting the expression of genes important in melanogenesis, at two levels:

- at an early stage, at the level of genes of which the products are involved in the synthesis of melanin and the formation of melanosomes,
- at a later stage, on genes of which the products are involved in the transport of melanosomes to the keratinocytes.

This dual mechanism enables a particularly effective inhibition of the synthesis of skin pigments, which inhibition induces an activity that is particularly beneficial as an active agent in compositions, such as cosmetic compositions, for reducing skin pigmentation defects or lightening the complexion.

The first objective claimed by this invention is an orchid extract of the *Brassocattleya Marcella* Koss species, obtained by the extraction of at least a part of said plant by means of a polar solvent or a mixture of polar solvents.

The plant material from which the extract according to the invention is obtained can include the entire plant or a part of the plant, and can in particular involve the leaves, flowers, stems, roots, fruit or mixtures formed by these various parts of the plant.

Preferably, the orchid part of this invention is chosen from among the stems or leaves of the *Brassocattleya marcella* Koss orchid. Even more preferably, the orchid part of this invention is a mixture of stems and leaves of the *Brassocattleya marcella* Koss orchid.

The plant or the parts of the plant selected can optionally be dried and/or ground.

According to a preferred embodiment of the invention, the plant material is in a dry, ground state.

The plant extract can be prepared by various extraction processes known to a person skilled in the art.

Advantageously, the extraction is preferably performed by placing the plant material selected in contact with a polar solvent or a mixture of polar solvents. According to this invention, the term "polar solvent" means that the solvent has a polarity index value equal to or greater than a value of 4. The polarity index is a quantity calculated on the basis of thermodynamic quantities (of solubility and change in state) indicating the more or less polar nature of a molecule. Reference can be made, for the solvent polarity indices, to the article of L. R. SNYDER: Classification of the solvent properties of common liquids; Journal of Chromatography, 92 (1974), 223-230, which is included by reference to this application.

The polar solvent is advantageously chosen from water, C1-C4 alcohols, such as ethanol, glycols, ethylene glycol, glycerol, butyleneglycol and propyleneglycol and mixtures thereof.

According to a preferred implementation of the invention, the extraction is performed by using a hydro-alcoholic mixture, in particular a water-ethanol mixture, and preferably a water-ethanol mixture, advantageously in a 50/50 (v/v) ratio.

According to another alternative of the invention, the extraction can also be performed by a process implementing a polar solvent in the subcritical state, in which said solvent is advantageously water in the subcritical state.

The extraction can also optionally include an additional step consisting of a treatment of the extract intended to partially or completely bleach it, or to purify it.

The extraction can be completed by a step of partially or entirely removing the extraction solvents.

In the event of a partial removal of the extraction solvents, the extract is generally concentrated until an aqueous concentrate free of significant amounts of organic solvent is obtained. In the case of total removal of these solvents, a dry residue is obtained.

Alternatively, the product of the extraction step can be lyophilized or atomized and be in the form of a powder.

The powder can be used as is in a composition, such as a cosmetic composition, according to the present invention, or be dispersed in a solvent or a mixture of solvents.

In general, the product of the extraction step can be dissolved or dispersed in a solvent or a mixture of solvents, in order to be used as an active agent in the compositions of the invention.

The solvent or the mixture of solvents in which the extract is dissolved or dispersed can be identical to or different from that used for the extraction.

The extract of the invention can also be adsorbed on a support advantageously chosen from nylon powders, porous or non-porous powders and micas or any inorganic laminar substance.

In this case, the extract used is preferably an extract in butylene glycol or an aqueous extract.

The second subject matter claimed by this invention is a composition, advantageously a cosmetic composition, comprising, as an active agent, an extract of the *Brassocattleya Marcella* Koss species, and at least one excipient, such as a cosmetically acceptable excipient.

Said composition includes an effective amount of orchid extract according to this invention in order to obtain the desired effect.

The orchid extract according to the invention is advantageously present as an active agent in the composition in a proportion ranging from 0.001 to 5% by weight of the composition, and preferably 0.1 to 1% by weight of the composition.

The composition according to the invention is advantageously intended for topical use.

The composition according to the invention can, for example, be a serum, a lotion, a spray, a foam, a solution, a powder, a pomade, a milk, an emulsion, a tinted cream or a hydrogel, preferably a mask, or it can be in the form of a stick or a patch.

The compositions including the orchid extract according to the invention advantageously include at least one other active agent, which is advantageously cosmetically acceptable.

Thus, the compositions that include the orchid extract according to the invention can also include one or more other active agents capable of being chosen from substances having a depigmenting activity or a skin lightening activity; substances having a weight loss activity; substances having a hydrating activity; substances having a calming, soothing or relaxing activity; substances having a skin microcirculation stimulating activity in order to improve the brightness of the complexion, in particular for the face; substances having a sebo-regulatory activity for care of oily skin; substances intended to clean or purify the skin; substances having an anti-radical activity; substances intended to attenuate or slow the effects of skin aging, in particular the formation of wrinkles, by an activity intended to promote maintenance of the skin structure and/or to limit the breakdown of the extracellular matrix of superficial layers of the dermis and the epidermis and/or to obtain a skin protective, corrective or restructuring effect; and substances having an anti-inflammatory activity.

It is particularly preferable to combine the orchid extract of the invention with active agents chosen from:

purified molecules or extracts promoting cell renewal, for example vitamin A, retinol or retinol esters; alpha or beta hydroxyacids (AHA) such as acids of fruits, malic, glycolic, citric or lactic acids, salicylic acid or esters thereof, gentisic acid or esters thereof, in particular tocopherol gentisate, purified molecules or extracts regulating epidermal differentiation such as ecdysteroids, ecdysterone, turkesterone or calcium derivatives, or vitamin D precursors, purified molecules or astringent extracts that shrink pores, such as hamamelis extracts or mushroom extracts classically used in cosmetics, anti-UVA and UVB radiation filters, such as benzophenone-4 butyl methoxydibenzoylmethane, ethylhexyl methoxycinnamate, octocrylene, ethyl hexyl salicylate, phenylbenzimidazole sulfonic acid, homosalate, alone or in combination with titanium oxides or not, purified molecules or extracts acting on pigmentation such as Kojic acid, kushenol B, liquorice root extracts, arbutin, calcium pantetheine sulfonate, boldine, diacetylboldine, stable derivatives of vitamin C, lilium extracts, in particular lilium candidum and in particular bulb extracts, soybean extracts, purified molecules or anti-radical extracts, *Artemisia Capillaris* extract, *Sanguisorba officinalis* extract, resveratrol and derivatives thereof, ergothioneine and derivatives thereof, thiotaurine, grape seed polyphenols, purified molecules or extracts promoting hyaluronic acid synthesis at the epidermal and dermal level, resulting in superbly hydrated and smoother skin, in particular an *Eriobotrya japonica* extract, or small fragments of hyaluronic acid.

According to a preferred embodiment of the invention, the composition includes, in addition to the orchid extract according to the invention, at least one other active agent preferably chosen from the group including boldine or one of the cosmetically acceptable derivatives thereof, in particular diacetylboldine, and/or a Lilium Candidum bulb extract, and/or adenosine.

Preferably, the composition includes, in addition to the orchid extract according to the invention, boldine.

Preferably, the composition includes, in addition to the orchid extract according to the invention, a boldine derivative, such as diacetyl boldine.

Preferably, the composition includes, in addition to the orchid extract according to the invention, boldine or diacetyl boldine, as well as a Lilium Candidum bulb extract. The mixture of the three compounds is advantageously used in a proportion of 0.5 to 10% by weight, and even more advantageously between 2 and 5% by weight of the total composition.

Preferably, the composition includes, in addition to the three compounds cited above, adenosine. The mixture of the four compounds is advantageously used in a proportion ranging from 0.5 to 10% by weight, and even more advantageously from 2 to 5% by weight of the total composition.

A particularly preferred composition is that combining the orchid extract according to the invention, which is present in a proportion ranging from 0.3 to 4% by weight of the composition, and boldine or diacetyl boldine, in a proportion ranging from 0.2 to 6% by weight of the composition.

Advantageously, the orchid and boldine or diacetyl boldine mixture is used in a proportion ranging from 0.5 to 10% by weight of the final composition, and preferably in a proportion ranging from 2 to 5%.

The composition according to the invention also advantageously includes at least one cosmetically acceptable excipient, which excipient can advantageously be chosen from polymers, surfactants, rheology control agents, fragrances, electrolytes, pH adjusters, antioxidants, preservatives, dyes, mother-of-pearl, pigments and mixtures thereof.

The third subject matter claimed by this invention is the use of the orchid extract described above as an active skin depigmenting agent, advantageously in a cosmetic composition.

The invention also relates to the use of the orchid extract described above to prepare a cosmetic composition such as an active skin depigmenting agent.

The extract is used in particular as an active agent in cosmetic compositions such as those described above.

The examples below, such as examples 3 to 6, provide formulations specifically designed to be used for homogenization of the skin pigmentation.

In a specific embodiment, the invention relates to the use of the orchid extract of the *Brassocattleya Marcella* Koss species as described above in a cosmetic composition or in the preparation of a cosmetic composition, in which said composition is intended to correct or attenuate skin pigment spots or the coloring of hyperpigmented skin areas; to attenuate the edge of depigmented areas caused by leucoderma; to improve the uniformity of the skin coloring; or to lighten the complexion.

According to a feature of this invention, the extract can advantageously be used in a cosmetic composition for correcting or attenuating skin pigment spots or the coloring of hyperpigmented skin areas, in particular those involving various skin discolorations, in particular:
- skin effects of photodermatoses,
- contact dermatoses, drug-induced photodermatoses, melasma, keratoses, for example senile or actinic keratosis,
- senile lentigo (age spots), solar lentigo,
- pigment spots resulting from scars or burns, or
- pigment spots caused by allergic or phototoxic reactions.

According to another feature of this invention, the extract can advantageously be used in a cosmetic composition for correcting or attenuating the edge or the periphery of depigmented areas caused by certain types of leucoderma, such as vitiligo.

The fourth subject matter claimed by this invention is a method for cosmetic care of the skin using the extract according to the invention and including the application, on at least one hyperpigmented area of the skin of the body or the face, of an effective amount of at least one cosmetic composition as defined above, including an orchid extract of the *Brassocattleya Marcella* Koss species as the cosmetic active agent, in order to correct or attenuate skin pigment spots or the coloring of said hyperpigmented area; in order to attenuate the edge of depigmented areas caused by leucoderma; or in order to homogenize the pigmentation of said skin area or lighten the complexion.

The examples below illustrate the invention without restricting the scope thereof.

EXAMPLE 1

Preparation of *Brassocattleya marcella* Koss Orchid Extracts

Extract 1: A stem and leaf extract with butylene glycol at 0.50% by weight is prepared by maceration for 24 hours, then filtered, cooled for 18 hours and filtered.

The filtrate is collected and tested for its depigmenting activity.

Extract 2: 50 g of fresh stems and leaves are macerated for 48 hours under gentle stirring at room temperature in a butylene glycol-water mixture in a ratio of 50/50.

The mixture is filtered, the filtrate is recovered and kept at 4° C. for 24 hours.

The filtrate is recovered in order to be tested for its depigmenting activity.

Extract 3: An extract is prepared from the shoots of stems and flowers of the plant by a hydro-alcoholic mixture preferably consisting of ethanol/water (70/30, v/v) at room temperature.

The solution obtained after filtration is concentrated with a rotary evaporator to 20% of the initial volume, then re-filtered.

The solution obtained can be used in compositions according to the invention, such as the cosmetic composition according to example 3.

Extract 4: The plant material consisting of leaves and stems of *Brassocattleya marcella* is heat-extracted by a water/ethanol (95/5, v/v) mixture for 20 minutes, then left to cool.

The solution is filtered, then lyophilized. The lyophilisate obtained is placed in butylene glycol and titrated at 1% dry weight.

This extract can be used in composition according to the invention, such as the cosmetic compositions according to examples 4 and 5.

EXAMPLE 2

Determination of the Activity of *Brassocattleya marcella* Koss Extract on Normal Human Melanocytes in Culture Cell Culture Normal human melanocytes (NHM) are obtained from healthy skin from plastic surgery.

The melanocytes are seeded in a 75 $cm^2$ flask in an amount of $10^6$ cells per flask in a proliferation medium at Invitrogen, namely K-SFM 90% supplemented with E199 containing 50 µg/mL of bovine pituitary extract, 5 ng/mL of EGF and 0.25 µg/mL of PdBu (phorbol 12,13-dibutyrate, Sigma).

When confluence is reached, the NHMs are rinsed 3 times with Phosphate Buffered Saline (PBS), trypsinized, seeded, then incubated in a Petri dish with a diameter of 100 mm until confluence.

Treatment by the extract according to the invention

The cells are treated for 4 or 24 hours, under different conditions:
- *Brassocattleya marcella* Koss extract at 1% (v/v) (extract 1 of example 1).
- Solvent (Butylene Glycol) 1% (v/v)=control After 4 or 24 hours of culture in the proliferation medium without PDBu (phorbol 12,13-dibutyrate), the total RNAs are extracted.

It was previously verified that the extract tested is non-cytoxoxic at the doses used by an MTT test.

Extraction of Total RNA

After incubation, the culture media are eliminated, then the cells are placed on an ice bed without rinsing first.

Under a chemical hood, the cells are mechanically separated and lyzed in 1 mL of RNAplus (QBiogene), then everything is collected in an Eppendorf tube.

After this, the total RNAs are assayed using a bioanalyzer and the RNA 6000 Nano LabChip Kit (Agilent).

Then, a reverse transcription step is performed on the total RNAs using the Applied Biosystem High Capacity cDNA archive kit in order to obtain the complementary DNAs.

The effect on the potential genes of interest is determined using the Taqman low-density array technology (TLDA of Applied Biosystems), which performs a multi-target PCR, thus enabling changes in gene expression to be determined quantitatively on a plurality of genes (additional details in L. V. Abruzzo et al., Biotechniques, 2005, 38, 785-792).

50 μL of each of the cDNAs are mixed with 50 μL of "Universal Master Mixt" buffer, and the 100 μL obtained are deposited on the microfluidic card-type DNA chip.

It is centrifuged twice in succession at 1200 g, then the cDNA deposition line is cut, and introduced into the TLDA HT 7900 apparatus (Applied Biosystems), which performs a PCR.

We thus have access to the NHM gene expression profile as well as to its possible change under the effect of the treatment.

Results

Analysis after 4 hours of treatment of NHM cultures by a *Brassocattleya marcella* Koss extract at 1% (v/v) (extract 1 of example 1):

The *Brassocattleya marcella* Koss extract has the following in vitro effects:

Decrease in the activity of the AP3B2 gene (adaptor-related protein complex 3, beta-2 subunit) involved in the transfer of TRPs (Tyrosine Related Proteins), from the Trans Golgi Network (TGN) to the melanosomes. This transport step is essential to the activation and release of the TRPs in the melanosomes (cf. Pigment Cell Res 13: 222-29, 2000).

Decrease in the activity of the GPR143 gene (G Protein-coupled Receptor 143), which codes for a receptor coupled to a protein G involved in the formation and transport of melanosomes (cf. Pigment Cell Res 18: 227-233, 2005).

Decrease in the activity of the VAMP 2 gene (Vesicle-Associated Membrane Protein) or synaptobrevin 2 coding for a SNARE protein also involved in the transport of melanosomes (cf. Traffic 7: 769-78, 2006).

Decrease in the activity of the TYR gene coding for tyrosinase, an enzyme involved in the first phases of melanin synthesis (cf. Physiol Rev 84: 1155-1228, 2004).

Decrease in the activity of the SILV gene coding for the proteins gp100 and Pme117, early markers of melanosomes, involved in the maturation thereof (polymerization of DiHydroxyIndole Carboxylic Acid into melanin) (cf. Physiol Rev 84: 1155-1228, 2004).

Analysis after 24 hours of treatment of NHM by a 1% *Brassocattleya marcella* Koss extract (extract 1 of example 1):

The *Brassocattleya marcella* Koss extract has the following effects in vitro:

decrease in the activity of the AP3M2 gene, another isoforms of AP3, decrease in the activity of the MC1R gene, decrease in the activity of the STOML2 gene, another gene coding for a protein of the SNARE family, involved in the peripheral membrane localization of melanosomes via membrane fusion for exocytosis thereof, and decrease in the activity of the SNAP 23 gene, involved in the exocytosis of melanosomes.

SNAP23, STOML2 and VAMP2 are co-localized at the melanosomes membrane and participate in the fusion of 10 the melanosome and plasma membranes (cf. Traffic 7: 769-78, 2006).

Conclusion on Biological Activity

The *Brassocattleya marcella* Koss extract has a skin pigmentation inhibiting activity, by acting both on the synthesis of melanin and on the transport and transfer of melanosomes.

Indeed, in this experiment, the following effects are observed:

Action at 4 hours on the mechanisms involved in the early steps of melanogenesis (synthesis of melanin, formation and transport of melanosomes in the dendrites);

Action at 24 hours in the subsequent steps of pigmentation, in particular on the transfer of melanosomes carrying melanin to the neighboring keratinocytes.

These two modes of action are complementary throughout the melanin synthesis and transfer chain and are thus an ingredient of the highest interest for use as an active agent in cosmetic compositions intended to lighten the complexion and/or fight skin pigmentation defects.

EXAMPLE 3

Emulsion for Treating Facial Discoloration

An emulsion is prepared which includes the *Brassocattleya marcella* Koss extract, as prepared in example 1 (extract 3), and the following active agents (% expressed by weight):

| | |
|---|---|
| *Brassocattleya marcella* Koss extract | 3% |
| Sunflower seed extract | 2% |
| Hyaluronic acid | 2% |
| Glycols | 3% |
| Excipient | qsf 100% |

The cream is applied locally twice a day.

EXAMPLE 4

Cream for Treating the Skin Consequences of Photodermatosis

An emulsion is prepared, containing the *Brassocattleya marcella* Koss extract, as prepared in example 1 (extract 4), and the following active agents (% expressed by weight):

| | |
|---|---|
| *Brassocattleya marcella* Koss extract | 2% |
| Diacetyl boldine | 1% |
| *Lilium candidum* bulb extract | 2% |
| Glabridin | 0.5% |
| Adenosine | 0.1% |
| Ecdysterone | 0.2% |
| Lactic acid | 1% |
| Oat polysaccharides | 2% |
| Hyaluronic acid | 2% |
| Ammonium glycyrrhizinate | 0.1% |
| Ascorbyl glycoside | 2% |
| UVA + UVB filter | 5% |
| Excipients | qsf 100% |

The cream is applied locally in the morning and before any exposure to daylight.

EXAMPLE 5

Serum for Local Treatment of Reaction Hyperpigmentation

A serum is prepared, containing the *Brassocattleya marcella* Koss extract, as prepared in example 1 (extract 4), and the following active agents (% expressed by weight):

| | |
|---|---|
| *Brassocattleya marcella Koss* extract | 2.5% |
| Boldine | 0.1% |
| Diacetyl boldine | 2% |
| Ergothioneine | 0.1% |
| Kushenol | 0.2% |
| Tocopherol gentisate | 0.5% |
| Alcohol | 2% |
| Lactic acid | 1.5% |
| Excipient | qsf 100% |

The serum is applied locally using an applicator, then in the morning after 5 minutes, the cream according to example 4 is applied.

In the evenings, the serum is used twice at 20-minute intervals.

EXAMPLE 6

Treating and Concealing Foundation

The emulsion containing the following active agents (% expressed by weight) is prepared:

| | |
|---|---|
| *Brassocattleya marcella Koss* extract | 1% |
| Diacetyl boldine | 1% |
| Adenosine | 1% |
| UVB filter | 2% |
| Titanium dioxide | 2% |
| Tocopherol acetate | 0.5% |
| Excipient containing colored pigments | qsf 100% |

The foundation is applied as facial make-up after use of the serum according to example 5 or the cream according to example 4.

The invention claimed is:

1. A cosmetic composition comprising, as active agents, (i) an orchid extract of the *Brassocattleya marcella* Koss species, wherein said extract is obtained by extraction of at least a part of said plant using a polar solvent or a mixture of polar solvents; and
   (ii) boldine or a cosmetically acceptable derivatives thereof, and at least one cosmetically acceptable excipient.

2. The composition according to claim 1, wherein said orchid extract is present in a proportion ranging from 0.001 to 5% by weight of the composition.

3. The composition according to claim 2 wherein said orchid extract is present in a proportion of 0.1 to 1% by weight of the composition.

4. The composition according to claim 1, wherein said boldine derivative is diacetyl boldine.

5. The composition according to claim 1, wherein the extracted part of said orchid is chosen from among the stems, the leaves and a mixture of stems and leaves of the orchid.

6. The composition according to claim 1, wherein the polar solvent is chosen from among water, $C_1$-$C_4$ alcohols, glycols and mixtures thereof.

7. The composition according to claim 6, wherein $C_1$-$C_4$ alcohol is ethanol.

8. The composition according to claim 6, wherein glycol is chosen in the group consisting of ethylene glycol, glycerol, butyleneglycol and propyleneglycol.

9. The composition according to claim 1, wherein the polar solvent is a hydro-alcoholic mixture.

10. The composition according to claim 1, wherein the polar solvent is a water-ethanol mixture.

11. The composition according to claim 1, wherein the polar solvent is a water-ethanol mixture in a 50/50 (v/v) ratio.

12. A cosmetic composition comprising, as active ingredients, an orchid extract of the *Brassocattleya marcella* Koss species, wherein said composition comprises:
    (a) a *Brassocattleya marcella* Koss extract;
    (b) diacetyl boldine; and
    (c) a *Lilium candidum* bulb extract.

13. Cosmetic care method for correcting or attenuating skin hyperpigmentation or the coloring of a hyperpigmented skin area; homogenizing the pigmentation of said hyperpigmented skin area or lightening the complexion of the skin; or attenuating the edge of depigmented areas caused by leucoderma;
    which comprises the application of an effective amount of the cosmetic composition according to claim 1, on at least one hyperpigmented area of the skin of the body or the face in need thereof.

* * * * *

UNITED STATES PATENT AND TRADEMARK OFFICE
CERTIFICATE OF CORRECTION

PATENT NO. : 8,414,933 B2
APPLICATION NO. : 12/382251
DATED : April 9, 2013
INVENTOR(S) : Jean-Christophe Archambault et al.

It is certified that error appears in the above-identified patent and that said Letters Patent is hereby corrected as shown below:

IN THE SPECIFICATION

Column 7, line 45, please insert the following paragraph:

-- Decrease in the activity of the MC1R gene, which regulates the action of the pro-pigmenting MSH (Melanocyte Stimulating Hormone) (cf. Physiol Rev 84:1155-1228, 2004). --.

Column 7, lines 64-66 from the bottom, please replace "SNAP23, STOML2 and VAMP2 are co-localized at the melanosomes membrane and participate in the fusion of 10 the melanosome and plasma membranes" with -- SNAP23, STOML2 and VAMP2 are co-localized at the melanosomes membrane and participate in the fusion of the melanosome and plasma membranes --.

Signed and Sealed this
Thirteenth Day of August, 2013

Teresa Stanek Rea
*Acting Director of the United States Patent and Trademark Office*